(12) United States Patent
Bertuch et al.

(10) Patent No.: US 12,055,607 B2
(45) Date of Patent: Aug. 6, 2024

(54) CABLE MANTLE FOR SHIELD CURRENT SUPPRESSION IN A SHIELDED CABLE

(71) Applicant: Fraunhofer-Gesellschaft zur Förderung der angewandten Forschung e.V., Munich (DE)

(72) Inventors: Thomas Bertuch, Wachtberg-Werthhoven (DE); Diego Betancourt, Wachtberg-Werthhoven (DE); Jürgen Jenne, Bremen (DE); Matthias Guenther, Bremen (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 360 days.

(21) Appl. No.: 17/131,360

(22) Filed: Dec. 22, 2020

(65) Prior Publication Data
US 2021/0199735 A1    Jul. 1, 2021

(30) Foreign Application Priority Data
Dec. 27, 2019   (EP) ..................................... 19219837

(51) Int. Cl.
| | | |
|---|---|---|
| *G01R 33/28* | (2006.01) | |
| *A61B 5/00* | (2006.01) | |
| *A61B 5/055* | (2006.01) | |
| *H01B 11/18* | (2006.01) | |
| *H02G 3/04* | (2006.01) | |

(52) U.S. Cl.
CPC .......... *G01R 33/288* (2013.01); *A61B 5/0033* (2013.01); *A61B 5/055* (2013.01); *H01B 11/1895* (2013.01); *H02G 3/0481* (2013.01)

(58) Field of Classification Search
CPC ..... G01R 33/288; A61B 5/0033; A61B 5/055; H01B 11/1895; H02G 3/0481
See application file for complete search history.

(56) References Cited

U.S. PATENT DOCUMENTS

| | | |
|---|---|---|
| 6,605,775 B1 | 8/2003 | Seeber et al. |
| 9,160,295 B2 | 10/2015 | Waks et al. |
| 10,790,564 B2 * | 9/2020 | Tkadlec .................... H01P 7/04 |

(Continued)

*Primary Examiner* — Dixomara Vargas
(74) *Attorney, Agent, or Firm* — Perkins Coie LLP; Michael A. Glenn

(57) ABSTRACT

A cable mantle for shield current suppression in a shielded cable includes a through hole for hosting the shielded cable; and a plurality of resonant elements; wherein each of the resonant elements includes an inner tube-shaped conductive structure; an outer tube-shaped conductive structure; a first transversal conductive structure; a second transversal conductive structure; and at least one capacitor bridging a gap between a first longitudinal portion of the outer tube-shaped conductive structure and a second longitudinal portion of the outer tube-shaped conductive structure, so that an electrical behavior of the inner tube-shaped conductive structure, the first longitudinal portion of the outer tube-shaped conductive structure, the second longitudinal portion of the outer tube-shaped conductive structure, the first transversal conductive structure, the second transversal conductive structure and the at least one capacitor is equivalent to a parallel resonant circuit defining a resonance frequency of the respective resonant element.

13 Claims, 10 Drawing Sheets

(56) References Cited

U.S. PATENT DOCUMENTS

| | | | |
|---|---|---|---|
| 2008/0297154 A1* | 12/2008 | Otake | G01R 33/34046 |
| | | | 324/318 |
| 2019/0140334 A1* | 5/2019 | Tkadlec | H01P 7/04 |
| 2019/0277926 A1* | 9/2019 | Stormont | G01R 33/54 |
| 2020/0408861 A1* | 12/2020 | Park | G01R 33/5659 |
| 2021/0022610 A1* | 1/2021 | Domnich | A61B 5/6862 |

* cited by examiner

CABLE MANTLE FOR SHIELD CURRENT SUPPRESSION IN A SHIELDED CABLE

CROSS-REFERENCE TO RELATED APPLICATION

This application claims priority from European Patent Application No. EP19219837.2, which was filed on Dec. 27, 2019, and is incorporated herein in its entirety by reference.

The present invention relates generally to shield current suppression in a shielded cable.

BACKGROUND OF THE INVENTION

Electrical transmission lines used for transmitting electronic signals susceptible to external electromagnetic noise often employ shielded cables comprising at least one conductive center wire and a conductive shield shielding the at least one conducting center wire. The conductive shield is grounded to prevent common mode signals. A common mode signal is defined as an unwanted current that occurs on the conductive shield or the ground, where the ground is considered to have zero potential.

In applications, where an intense electromagnetic field is present, unwanted shield currents may occur.

One of the methods of reducing shield current is the use of high-quality (Q) factor LC-tank circuits, also known as cable-traps. The inductance of this LC-tank is created by winding the shielded cable in one direction forming a helix. A capacitance is connected in parallel to the inductance to tune to the desired resonance frequency. Despite its simplicity, this method presents several disadvantages when applied to a shielded cable: i) An extra length in the cable may be used for the turns of the inductor, increasing this way the insertion losses of the carried signals; ii) The cable-trap changes, due to the extra length, the phase distance to the test equipment; iii) Manufacturing of cable-traps is cumbersome, involving modification of cables including the removal of portions of its external insulation for attaching the capacitor; iv) Optionally, the cable may need to be wound twice in opposite directions on two separate spools to prevent coupling to the external magnetic fields; v) The cable-trap cannot be easily repositioned along the shielded cable in order to find the optimal trap location, i.e., at the maximum current point or at a position where it does not disturb; and vi) it is only suitable for narrowband operations.

It is also known that ferrite "beads" can be used to reduce shield currents although they are unsuitable in areas of an intense magnetic field.

An alternative approach is introduced in the U.S. Pat. No. 6,605,775 B1 with the title "Floating radio frequency trap for shield currents". This Patent describes the effect of a unique floating shield current trap that provides first and second concentric tubular conductors electrically connected to provide a narrowband resonance-induced high impedance of current flow in a path consisting of the inner and outer conductors and their junctions thereby suppressing coupled current flow on a shield of a conductor contained within the first inner tubular conductor. An important drawback of this approach is the lack of broadband and multi-frequency features which through a unique element type in the system cannot be easily provided.

Another alternative approach is the apparatus and method for a radially attachable RF trap attached from a side to a shielded RF cable presented in the U.S. Pat. No. 9,160,295 B2, with the title "Snap-on coaxial cable balun and method for trapping RF current on outside shield of coax after installation". This invention describes some embodiments in which the RF trap creates a high impedance on the outer shield of the RF cable at a frequency of RF signals carried on at least one inner conductor of the cable. The RF-trap apparatus for blocking stray signals on a shielded RF cable that has a peripheral shield conductor and an inner conductor for carrying RF signals includes: a case; an LC circuit having a resonance frequency equal to RF signals carried on one of the inner conductors; projections that pierce the insulation and connect the LC circuit to the shield conductor; and an attachment device that fixes the case to the cable with the LC circuit electrically connected to the shield conductor of the shielded RF cable. Besides the lack of broadband and multi-frequency features, a clear disadvantage of this approach is that the cable-trap needs to have electrical contact with the cable shield implying a deterioration of the same.

SUMMARY

One embodiment may have a cable mantle for shield current suppression in a shielded cable; wherein the cable mantle has a through hole along a longitudinal direction of the cable mantle, wherein the through hole is configured for hosting the shielded cable; wherein the cable mantle has a plurality of resonant elements arranged along the longitudinal direction of the cable mantle; wherein each of the resonant elements may have: an inner tube-shaped conductive structure, which extends in the longitudinal direction between a first end section of the resonant element and a second end section of the resonant element, and which surrounds in a circumferential direction a longitudinal portion of the through hole; an outer tube-shaped conductive structure, which extends in the longitudinal direction between the first end section of the resonant element and the second end section of the resonant element, and which surrounds in the circumferential direction a longitudinal portion of the inner tube-shaped conductive structure, wherein the outer tube-shaped conductive structure has a circumferential gap so that a first longitudinal portion of the outer tube-shaped conductive structure is separated from a second longitudinal portion of the outer tube-shaped conductive structure; a first transversal conductive structure, which connects the inner tube-shaped conductive structure and the first longitudinal portion of the outer tube-shaped conductive structure at the first end section of the resonant element; a second transversal conductive structure, which connects the inner tube-shaped conductive structure and the second longitudinal portion of the outer tube-shaped conductive structure at the second end section of the resonant element; and at least one capacitor bridging the gap between the first longitudinal portion of the outer tube-shaped conductive structure and the second longitudinal portion of the outer tube-shaped conductive structure, so that an electrical behavior of the inner tube-shaped conductive structure, the first longitudinal portion of the outer tube-shaped conductive structure, the second longitudinal portion of the outer tube-shaped conductive structure, the first transversal conductive structure, the second transversal conductive structure and the at least one capacitor is equivalent to a parallel resonant circuit defining a resonance frequency of the respective resonant element.

According to another embodiment, a cable arrangement may have:
at least one cable mantle for shield current suppression in a shielded cable;

wherein the cable mantle has a through hole along a longitudinal direction of the cable mantle, wherein the through hole is configured for hosting the shielded cable;

wherein the cable mantle has a plurality of resonant elements arranged along the longitudinal direction of the cable mantle;

wherein each of the resonant elements may have an inner tube-shaped conductive structure, which extends in the longitudinal direction between a first end section of the resonant element and a second end section of the resonant element, and which surrounds in a circumferential direction a longitudinal portion of the through hole;

an outer tube-shaped conductive structure, which extends in the longitudinal direction between the first end section of the resonant element and the second end section of the resonant element, and which surrounds in the circumferential direction a longitudinal portion of the inner tube-shaped conductive structure, wherein the outer tube-shaped conductive structure has a circumferential gap so that a first longitudinal portion of the outer tube-shaped conductive structure is separated from a second longitudinal portion of the outer tube-shaped conductive structure;

a first transversal conductive structure, which connects the inner tube-shaped conductive structure and the first longitudinal portion of the outer tube-shaped conductive structure at the first end section of the resonant element;

a second transversal conductive structure, which connects the inner tube-shaped conductive structure and the second longitudinal portion of the outer tube-shaped conductive structure at the second end section of the resonant element; and at least one capacitor bridging the gap between the first longitudinal portion of the outer tube-shaped conductive structure and the second longitudinal portion of the outer tube-shaped conductive structure, so that an electrical behavior of the inner tube-shaped conductive structure, the first longitudinal portion of the outer tube-shaped conductive structure, the second longitudinal portion of the outer tube-shaped conductive structure, the first transversal conductive structure, the second transversal conductive structure and the at least one capacitor is equivalent to a parallel resonant circuit defining a resonance frequency of the respective resonant element; and a shielded cable having at least one conductive center wire and a conductive shield shielding the at least one conductive center wire, wherein the at least one conductive center wire is isolated from the conductive shield, wherein the shielded cable is hosted in the through hole of the at least one cable mantle.

Another embodiment may have a system for examining an object, wherein the system has a magnetic resonance imaging scanner for a production of a magnetic resonance image of the object in an imaging volume, wherein the magnetic resonance imaging scanner has a magnet assembly for applying a static magnetic field to the imaging volume during the production of the magnetic resonance image, wherein the magnetic resonance imaging scanner has a radiofrequency coil assembly for applying a radiofrequency magnetic field to the imaging volume during the production of the magnetic resonance image, wherein the system has a monitoring device for monitoring the object in the imaging volume during the production of the magnetic resonance image, wherein the monitoring device has a sensing unit, an evaluating unit and a cable arrangement, wherein the sensing unit is configured for producing sensing signals related to the object during the production of the magnetic resonance image while being arranged within the imaging volume, wherein the evaluating unit is configured for evaluating the sensing signals, wherein the sensing signals are transmitted from the sensing unit to the evaluating unit by the cable arrangement, wherein the cable arrangement is configured as specified above.

Yet another embodiment may have a system for examining an object, wherein the system has a magnetic resonance imaging scanner for a production of a magnetic resonance image of the object in an imaging volume, wherein the magnetic resonance imaging scanner has a magnet assembly for applying a static magnetic field to the imaging volume during the production of the magnetic resonance image, wherein the magnetic resonance imaging scanner has a radiofrequency coil assembly for applying a radiofrequency magnetic field to the imaging volume during the production of the magnetic resonance image, wherein the system has a treating device for treating the object in the imaging volume during the production of the magnetic resonance image, wherein the treating device has an actuator unit, a control unit and a cable arrangement, wherein the control unit is configured for producing control signals, wherein the actuator unit is configured for applying energy to the object during the production of the magnetic resonance image while being arranged within the imaging volume depending on the control signals, wherein the control signals are transmitted from the control unit to the actuator unit by the cable arrangement, wherein the cable arrangement is configured as specified above.

The present invention provides a high impedance Electromagnetic Band Gap (EBG) structure formed by the concatenation of a plurality of resonant elements, which are configured to work cooperatively, to form a cable mantle (or cable jacket) to cover a shielded cable to suppress coupled shield currents in the presence of strong magnetic fields.

The inner tube-shaped conductive structure, the outer tube-shaped conductive structure, first transversal conductive structure and/or second transversal conductive structure of each of the resonant elements may be produced by using 3D printing techniques. The inner tube-shaped conductive structure, the outer tube-shaped conductive structure, first transversal conductive structure and/or second transversal conductive structure of each of the resonant elements may be manufactured from any conductive material such as metals or conductive polymers.

The inner tube-shaped conductive structure may be a cylindrical structure and the outer tube-shaped conductive structure may be a cylindrical structure which is divided into two pieces leaving a gap in between. The first transversal conductive structure may be a first radially extending metallic wall and the transversal conductive structure may be a second radially extending metallic wall.

The advantageous method for the realization of this invention in each of their advantageous embodiments is through the individual fabrication of the resonant elements.

Once all resonant elements are finished, they may be assembled following the advantageous embodiment alternative to create a cable mantle. Fabrication methods for the inner tube-shaped conductive structure, the outer tube-shaped conductive structure, first transversal conductive structure and/or second transversal conductive structure of each of the resonant elements include Computer Numerical Control (CNC) machinery for fabrication based on bulk metal, as well as, Additive Manufacturing (AM) techniques for fabrication based on laser sintering of metal powder/plastics. Lightweight embodiments are achieved by using plastics structures which are then metalized in a post-processing step. Advantageous plastic metallization methods include galvanization, sputtering and coating.

The capacitor is a passive electronic component with two terminals, wherein one of the terminals may be mounted to the first longitudinal portion of the outer tube-shaped conductive structure and wherein the other of the terminals may be mounted to the second longitudinal portion of the outer tube-shaped conductive structure, for example by using soldering techniques. The capacitor in particular may be an SMD-device.

The invention avoids an extra length for forming a helix in the shielded cable as well as a phase shift caused by such extra length. No modification at the shielded cable is necessary. The cable mantle may cover the whole length of the shielded cable or only a part of it. In the latter case, the cable mantle may be positioned at the optimal location or at a position where it does not disturb. Also, the cable mention may be repositioned easily.

The desired resonance frequency of each of the resonant element may be achieved by choosing appropriate dimensions for the inner tube-shaped conductive structure, the outer tube-shaped conductive structure, first transversal conductive structure and second transversal conductive structure and by choosing a capacitor having an appropriate capacitance. In particular, or different resonant elements may have different resonant frequencies Thus, the cable mantle according to the invention is suitable for a wide range of frequency. In particular, it is suitable for narrowband frequency operation, for broadband frequency operation as well as for multiple-frequency operation. This will be discussed below in more detail.

The present invention reduces the current along the shield of a shielded cable without electrical attachment to the cable itself, only by covering it.

The resonant elements may be surrounded by an outer mantle, which may be configured for connecting the individual resonant elements of the cable mantle and/or for protecting the individual resonant elements of the cable mantle. The outer mantle may be manufactured from a flexible polymer so that the cable mantle as a whole does not affect the flexibility of the shielded cable contained within.

In magnetic resonance imaging (MRI) applications, where an intense electric/magnetic field is present, shield currents can affect coil tuning, coil-to-coil coupling in phased array coils, image inhomogeneity, and most importantly can cause serious patient burns. Other undesired effects may include coil to shield iterations, coupling to other resonant circuits in the system, or coupling to an external case. A typical field strength for clinical scanners ranges from 0.2 Tesla to 3 Tesla. Typical field strengths used in research are even higher, for example 7 Tesla, 9.4 Tesla and 11 Tesla. Usually, the frequency of the MRI-scanner is derived from the field strength by multiplying the field strength in Tesla by 42.58 MHz/Tesla, so that the frequency is, for example, ~64 MHz at 1.5 Tesla and ~128 MHz at 3 Tesla. Some manufacturers are using field strengths of 2.9 Tesla yielding a frequency of ~123 MHz.

On the other hand, novel treatment methods in MRI foresee the use of external medical diagnosis equipment during the MRI scanning process in order to complement and improve the diagnosis, e.g., by the use of ultrasound scanners. Such external equipment needs to be compatible with MRI devices and therefore MRI compatible cables may be used in order to suppress coupled shield currents. The cable mantle according to the invention provides an excellent shield current suppression and may easily be adapted to the frequency of an MRI-device by adapting the resonance frequencies of the resonant elements to the frequency of an MRI-device. Thus, the cable mantle according to the invention is particularly suitable for a shielded cable which is used as part of secondary medical diagnosis equipment within the imaging volume of an MRI equipment.

The cable mantle according to the invention also may be used in other medical applications and for measurement of characteristics or installation of balanced or electrically small antennas.

The effect of the cable mantle according to the invention is to reduce coupled shield currents on a cable. The advantages are i) the mantle/jacket cable may be reusable and reconfigurable; ii) possible multi-frequency capabilities and iii) possible broad bandwidth behavior, iv) the cable mantle may be very compact, v) the flexibility of the covered shielded cable may be maintained.

According to some embodiments the resonant elements are arranged in a repetitive pattern, wherein a step size of the repetitive pattern is shorter than wavelengths corresponding to the resonance frequencies of the resonant elements.

In such embodiments each resonant element is designed to be as compact as possible, meaning each resonant element is electrically short compared with the wavelength of the operational frequency. By arranging the multiple resonant elements in repetitive patterns at scales that are smaller than the wavelength of the phenomena they influence, an electromagnetic band gap structure is formed which shows a "metamaterial" behavior.

The term "metamaterial" has been used to describe composite materials with features not readily available in nature. Electromagnetic band gap structures are broadly classified as metamaterials due to their unique band gap feature and high impedance properties. In this regard, some embodiments are based on a metamaterial approach design to create a cable mantle composed by electrically small resonant elements which are repetitively arranged and cooperatively interact to create a high impedance structure to prevent the current propagation along the shield of a shielded cable.

According to some embodiments the resonance frequencies of all of the resonant elements are equal. Such embodiments involve the concatenation of N resonant elements (N>1) tuned to the same resonance frequency to achieve a high quality-factor (Q) and a high impedance at the resonance frequency. The cable mantle may be as long as the shielded cable contained within but can vary its length according to specific application necessities and cover only segments of the cable. Such embodiments are especially suitable for narrowband applications. In particular, such embodiments are suitable for magnetic resonance imaging scanners which work at the single frequency. For example, if the magnetic resonance imaging scanner works with 64 MHz at 1.5 Tesla, all resonant elements may be tuned to 64 MHz.

According to some embodiments the resonant elements are grouped into a plurality of resonant element groups, wherein the resonance frequencies of all of the resonant elements of one of the resonant element groups are equal, wherein the resonance frequencies of the resonant elements of one of the resonant element groups are different from the resonance frequencies of the resonant elements of one other of the resonant element groups. Such embodiments imply the concatenation of N resonant elements that are grouped to configure M (M>1) different resonant element groups. Each resonant element group contains $k_i$ resonant elements following the relation $\Sigma_{i=1}^{M} k_i = N$. In order to set a multi-frequency response in the embodiment, each of the M resonant element groups of resonant elements is tuned to a different resonant frequency and all of the resonant elements of the same resonant element group are tuned to a same resonant frequency, which makes the cable mantle compatible with several standards, e.g. for 1 Tesla, 1.5 Tesla and 3 Tesla MRI scanners, in an unique embodiment at the same time. In this way a multi-frequency cable mantle is created. The resonant element group frequency tuning is made either by changing the dimensions of the resonant elements of that least one of the resonant element groups, by changing the capacitance associated to the resonant elements of at least one of the resonant element groups and/or by other suitable approaches.

According to some embodiments the resonance frequencies of at least some of the resonant elements are different, wherein the resonance frequencies of all of the resonant elements are distributed around a center resonance frequency with a maximum deviation of plus or minus 5%.

An additional alternative embodiment implies the concatenation of at least N resonant elements (N>1), wherein the resonance frequencies of at least some of the resonant elements differ slightly. By these features the bandwidth of the cable mantle may be enhanced. In an initial step, all unitary elements may be tuned to resonate at the center resonance frequency, and later, a small frequency shift is applied to each resonant element to create a broad-bandwidth behavior. The frequency shift follows either a random or a predefined distribution. The frequency deviation can be close to the central resonance frequency, a frequency shift of only a few MHz at each resonant element along the cable mantle is advantageous. The center resonance frequency may be equivalent to the nominal frequency of the MRI device. For example, the center resonance frequency may be 128 MHz for a 3 Tesla MRI equipment. The resonant elements are frequency shifted by changing their size dimensions, by employing different capacitors or by any other suitable method.

According to some embodiments the resonant elements are grouped into a plurality of resonant element groups, wherein the resonance frequencies of at least some of the resonant elements within each of the resonant element groups are different, wherein the resonance frequencies of the resonant elements within each of the resonant element groups are distributed around a center resonance frequency with a maximum deviation of plus or minus 5%, wherein the center resonance frequency of at least one of the resonant element groups is different from the center resonance frequency of one other of the resonant element groups.

Such embodiments contemplate a mixed behavior based on the aforementioned alternative embodiments, i.e. a broad-bandwidth and multi-frequency cable mantle. This alternative embodiment implies the concatenation of at least N resonant elements grouped in M resonant element groups (M>1). Each resonant element group contains $k_i$ resonant elements following the relation $\Sigma_{i=1}^{M} k_i = N$. In an initial step, the multi-frequency response in the embodiment may be set by tuning each of the M groups to a different center resonance frequency. In a second step, a broad-bandwidth behavior may be obtained by adding small but different frequency shifts to each of the resonant elements belonging to the M-th subgroup. For example, the resonant elements of a first resonant element group could be tuned around a central resonant frequency of 32 MHz, the resonant elements of a second resonant element group could be tuned around a central resonant frequency of 64 MHz and the resonant elements of a third resonant element group could be tuned around a central resonant frequency of 128 MHz.

According to some embodiments the at least one capacitor of one of the resonant elements is a variable capacitor. Such features allow adapting the resonant frequencies of the resonant elements in order to adapt the cable mantle to different applications. The variable capacitor may be a trimmer capacitor.

According to some embodiments the cable mantle comprises a first construction group and a second construction group, wherein the first construction group and the second construction group are connectable to each other in a detachable way, wherein the shielded cable can be transversally moved into the cable mantle or transversally removed from the cable mantle respectively when the first construction group and the second construction group are detached from each other.

In such embodiments the cable mantles may be divided into two construction groups. A splitting plane may be defined by a longitudinal axis and a transversal axis of the cable mantle. These features imply a convenient detachable function, which allows mounting the cable mantle to a shielded cable or removing the cave amended from the shielded cable respectively in an easy way. The cable mantle may comprise a snap-on connection. However, the two construction groups may be connected to each other by other suitable means.

According to some embodiments at least neighboring resonant elements of the plurality of resonant elements are spaced apart from each other. These features enhance the flexibility of the cable mantle.

In a further aspect the invention provides a cable arrangement comprising at least one cable mantle according to the invention and a shielded cable comprising at least one conductive center wire and a conductive shield shielding the at least one conductive center wire, wherein the at least one conductive center wire is isolated from the conductive shield, wherein the shielded cable is hosted in the through hole of the at least one cable mantle.

Generally spoken, the invention provides a flexible cable arrangement created with multiple resonant elements assembled together to increase the longitudinal impedance at one or multiple resonance frequencies and to enhance the operational bandwidth thereby suppressing coupled shield currents along the outside of the metallic shielding of the shielded cable. In particular, the shielded cable may be a coaxial cable comprising a conductive center wire and a conductive shield which are coaxially arranged.

According to some embodiments the at least one conductive center wire and the conductive shield of the shielded cable are insulated from the plurality of resonant elements of the at least one cable mantle. Such features allow using standardized shielded cables comprising an outer insulation without modifying the odd insulation.

In a further aspect the invention provides a system for examining an object, wherein the system comprises a magnetic resonance imaging scanner for a production of a magnetic resonance image of the object in an imaging volume, wherein the magnetic resonance imaging scanner comprises a magnet assembly for applying a static magnetic field to the imaging volume during the production of the magnetic resonance image, wherein the magnetic resonance imaging scanner comprises a radiofrequency coil assembly for applying a radiofrequency magnetic field to the imaging volume during the production of the magnetic resonance image, wherein the system comprises a monitoring device for monitoring the object in the imaging volume during the production of the magnetic resonance image, wherein the monitoring device comprises a sensing unit, evaluating unit and a cable arrangement, wherein the sensing unit is configured for producing sensing signals related to the object during the production of the magnetic resonance image while being arranged within the imaging volume, wherein the evaluating unit is configured for evaluating the sensing signals, wherein the sensing signals are transmitted from the sensing unit to the evaluating unit by the cable arrangement, wherein the cable arrangement is configured according to the invention.

The monitoring device may be an ultrasound imaging device, a video device or a physiological monitoring unit such as a motion tracker, an electrocardiograph (ECG), a magnetoencephalograph (MEG) or an electroencephalograph (EEG).

In a further aspect the invention provides a system for examining an object, wherein the system comprises a magnetic resonance imaging scanner for a production of a magnetic resonance image of the object in an imaging volume, wherein the magnetic resonance imaging scanner comprises a magnet assembly for applying a static magnetic field to the imaging volume during the production of the magnetic resonance image, wherein the magnetic resonance imaging scanner comprises a radiofrequency coil assembly for applying a radiofrequency magnetic field to the imaging volume during the production of the magnetic resonance image, wherein the system comprises a treating device for treating the object in the imaging volume during the production of the magnetic resonance image, wherein the treating device comprises an actuator unit, a control unit and a cable arrangement, wherein the control unit is configured for producing control signals, wherein the actuator unit is configured for applying energy to the object during the production of the magnetic resonance image while being arranged within the imaging volume depending on the control signals, wherein the control signals are transmitted from the control unit to the actuator unit by the cable arrangement, wherein the cable arrangement is configured according to the invention.

The treating device may be a focused ultrasound device for therapy or a guiding wire for catheters.

BRIEF DESCRIPTION OF THE DRAWINGS

Embodiments of the present invention will be detailed subsequently referring to the appended drawings, in which.

DETAILED DESCRIPTION OF THE INVENTION

Figure 1:
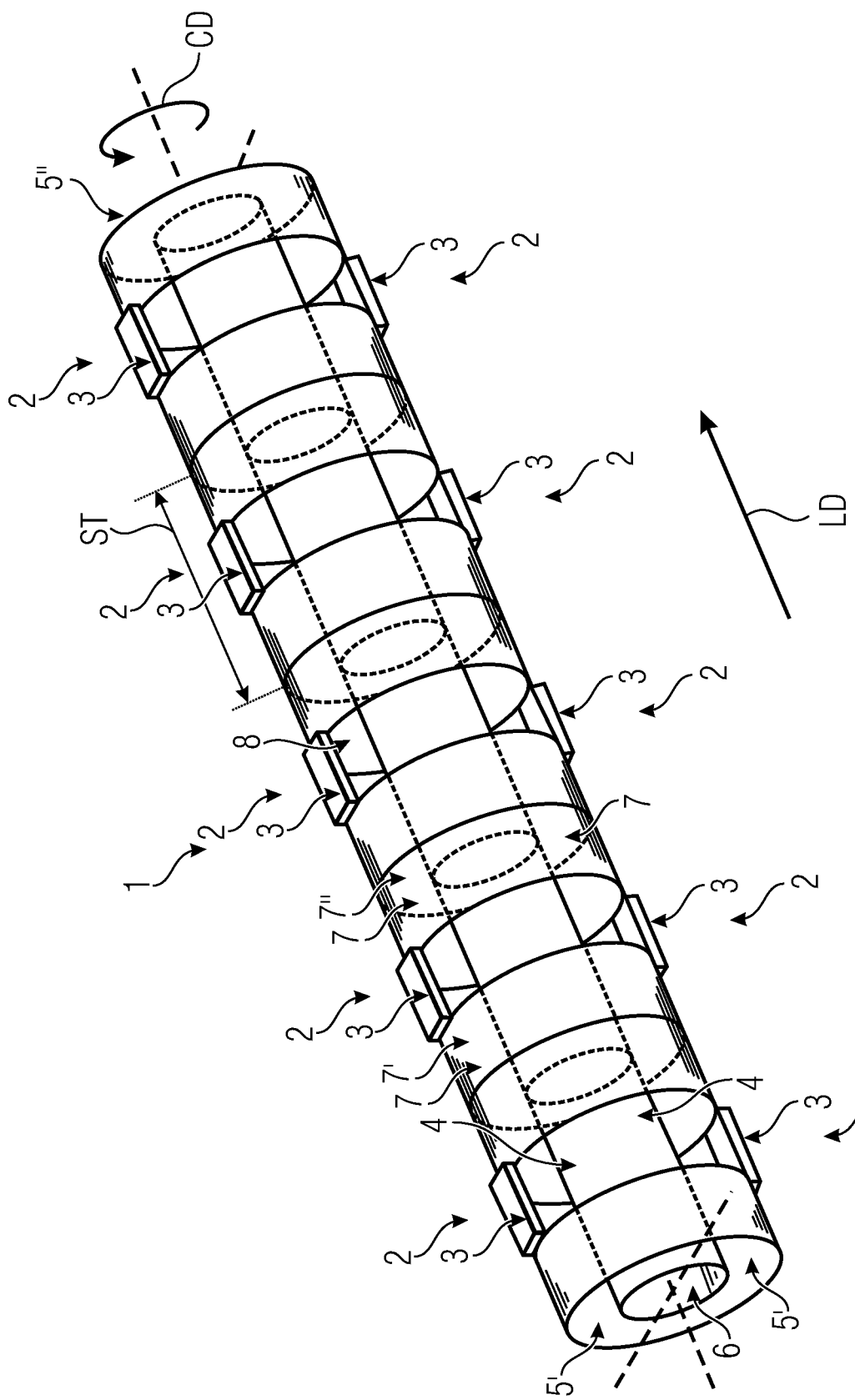
FIG. 1 illustrates an embodiment of a cable mantle according to the invention in a schematic three-dimensional view.

Equal or equivalent elements or elements with equal or equivalent functionality are denoted in the following description by equal or equivalent reference numerals.

In the following description, a plurality of details is set forth to provide a more thorough explanation of embodiments of the present invention. However, it will be apparent to those skilled in the art that embodiments of the present invention may be practiced without these specific details. In other instances, well-known structures and devices are shown in block diagram form rather than in detail in order to avoid obscuring embodiments of the present invention. In addition, features of the different embodiments described hereinafter may be combined with each other, unless specifically noted otherwise.

FIG. 1 illustrates an embodiment of a cable mantle 1 for shield current suppression in a shielded cable 20 according to the invention in a schematic three-dimensional view.

Figure 2:
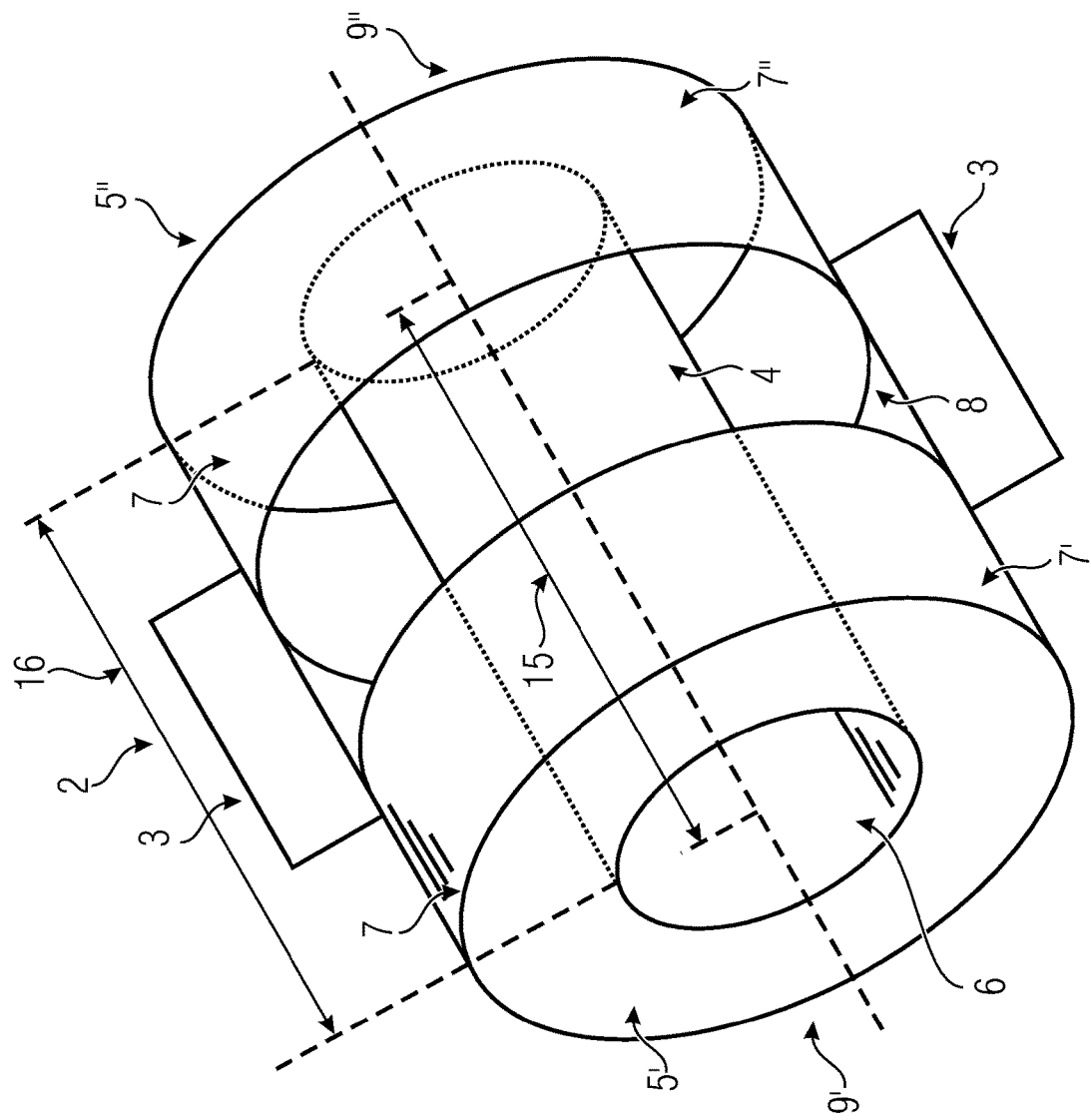
FIG. 2 illustrates an embodiment of a resonant element of a cable mantle according to the invention in a schematic three-dimensional view.

FIG. 2 illustrates an embodiment of a resonant element 2 of a cable mantle 1 for shield current suppression in a shielded cable 20 according to the invention in a schematic three-dimensional view.

The cable mantle 1 comprises a through hole 6 along a longitudinal direction LD of the cable mantle, wherein the through hole 6 is configured for hosting the shielded cable 20;

wherein the cable mantle 1 comprises a plurality of resonant elements 2 arranged along the longitudinal direction LD of the cable mantle 1;

wherein each of the resonant elements 2 comprises an inner tube-shaped conductive structure 4, which extends in the longitudinal direction LD between a first end section 9' of the resonant element 2 and a second end section 9" of the resonant element 2, and which surrounds in a circumferential direction CD a longitudinal portion 15 of the through hole 6;

an outer tube-shaped conductive structure 7, which extends in the longitudinal direction LD between the first end section 9' of the resonant element 2 and the second end section 9" of the resonant element 2, and which surrounds in the circumferential direction CD a longitudinal portion 16 of the inner tube-shaped conductive structure 4, wherein the outer tube-shaped conductive structure 7 comprises a circumferential gap 8 so that a first longitudinal portion 7' of the outer tube-shaped conductive structure 7 is separated from a second longitudinal portion 7" of the outer tube-shaped conductive structure 7;

a first transversal conductive structure 5', which connects the inner tube-shaped conductive structure 4 and the first longitudinal portion 7' of the outer tube-shaped conductive structure 7 at the first end section 9' of the resonant element 2;

a second transversal conductive structure 5'', which connects the inner tube-shaped conductive structure 4 and the second longitudinal portion 7'' of the outer tube-shaped conductive structure 7 at the second end section 9'' of the resonant element 2; and at least one capacitor 3 bridging the gap 8 between the first longitudinal portion 7' of the outer tube-shaped conductive structure 7 and the second longitudinal portion 7'' of the outer tube-shaped conductive structure 7, so that an electrical behavior of the inner tube-shaped conductive structure 4, the first longitudinal portion 7' of the outer tube-shaped conductive structure 7, the second longitudinal portion 7'' of the outer tube-shaped conductive structure 7, the first transversal conductive structure 5', the second transversal conductive structure 5'' and the at least one capacitor 3 is equivalent to a parallel resonant circuit defining a resonance frequency of the respective resonant element 2.

According to some embodiments the resonant elements 2 are arranged in a repetitive pattern, wherein a step size ST of the repetitive pattern is shorter than wavelengths corresponding to the resonance frequencies of the resonant elements 2.

According to some embodiments the at least one capacitor 3 of one of the resonant elements 2 is a variable capacitor.

FIG. 1 shows a perspective view of the cable mantle 1 which is assembled using a multitude of resonant elements 2 as shown in FIG. 2, wherein all of the resonant elements 2 have the same resonance frequency.

In FIG. 2 a perspective view of one of the resonant elements 2 is shown. The resonant element 2 contains an inner tube-shaped conductive structure 4 and an outer tube-shaped conductive structure 7. These structures 4 and 7 are electrically connected via a first transversal conductive structure 5' and a second transversal conductive structure 5'', which are placed at the extremes of the resonant element 2. A distance separation between resonant elements is possible. The distance separation may be achieved by a separate spacer (not shown) or as a spacer being a part of the resonant elements 2 (also not shown). The outer tube-shaped conductive structure 7 consists of a first longitudinal portion 7' of the outer tube shaped conductive structure 7 and a second longitudinal portion 7'' of the outer tube-shaped conductive structure 7. Capacitors 3 are placed between the circumferential gap 8 which separates the first longitudinal portion 7' of the outer tube shaped conductive structure 7 and the second longitudinal portion 7'' of the outer tube-shaped conductive structure 7. The through hole 6 of the unitary element 2 may be used to host a shielded cable.

Figure 3:
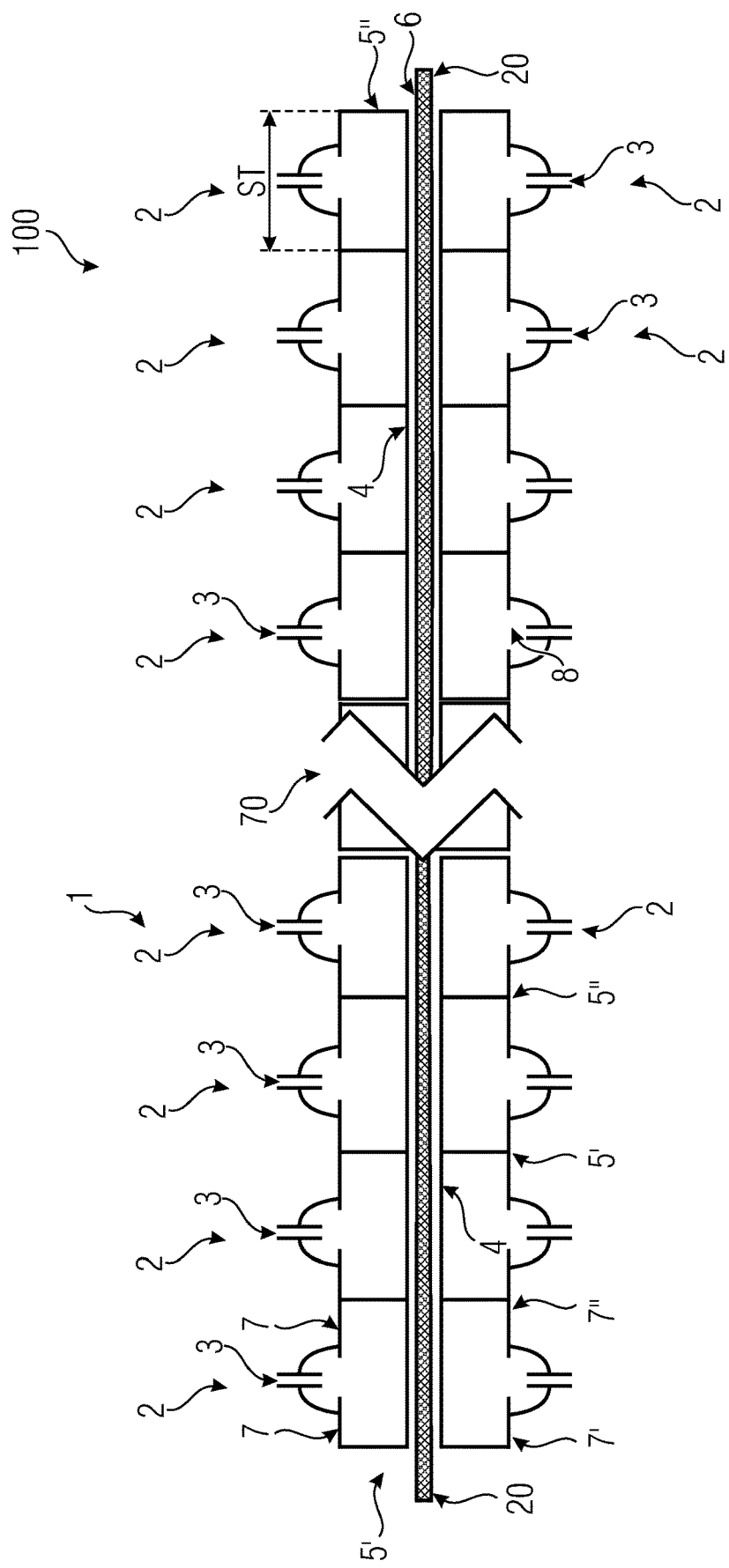
FIG. 3 illustrates a first embodiment of a cable arrangement according to the invention in a schematic view.

FIG. 3 illustrates a first embodiment of a cable arrangement 100 according to the invention in a schematic view.

The cable arrangement comprises at least one cable mantle 1 according to the invention and a shielded cable 20 comprising at least one conductive center wire and a conductive shield shielding the at least one conductive center wire, wherein the at least one conductive center wire is isolated from the conductive shield, wherein the shielded cable 20 is hosted in the through hole 6 of the at least one cable mantle 1.

According to some embodiments the at least one conductive center wire and the conductive shield of the shielded cable 20 are insulated from the plurality of resonant elements 2 of the at least one cable mantle 1.

According to some embodiments the resonance frequencies of all of the resonant elements 2 of the cable mantle 1 are equal.

According to some embodiments (not shown) at least some neighboring resonant elements 2 of the plurality of resonant elements 2 of the cable mantle 1 are spaced apart from each other.

In FIG. 3 a schematic diagram of an advantageous embodiment of the invention is shown. Herein, the cable mantle 1 is assembled using a multitude of resonant elements 2 to cover completely a shielded cable 20. Each resonant element 2 comprises an inner tube-shaped conductive structure 4 and an outer tube-shaped conductive structure 7. These structures 4 and 7 are electrically connected via a first transversal conductive structure 5' and a second transversal conductive structure 5'', which are placed at the extremes of the resonant element 2. The outer tube-shaped conductive structure 7 consists of a first longitudinal portion 7' of the outer tube shaped conductive structure 7 and a second longitudinal portion 7'' of the outer tube-shaped conductive structure 7. Capacitors 3 are placed between the circumferential gap 8 which separates the first longitudinal portion 7' of the outer tube shaped conductive structure 7 and the second longitudinal portion 7'' of the outer tube-shaped conductive structure 7. The through hole 6 of the unitary element 2 is used to host the shielded cable 20. The concatenation of such resonant elements 2 covers completely a long cable 20 here represented using a break 70.

Figure 4:
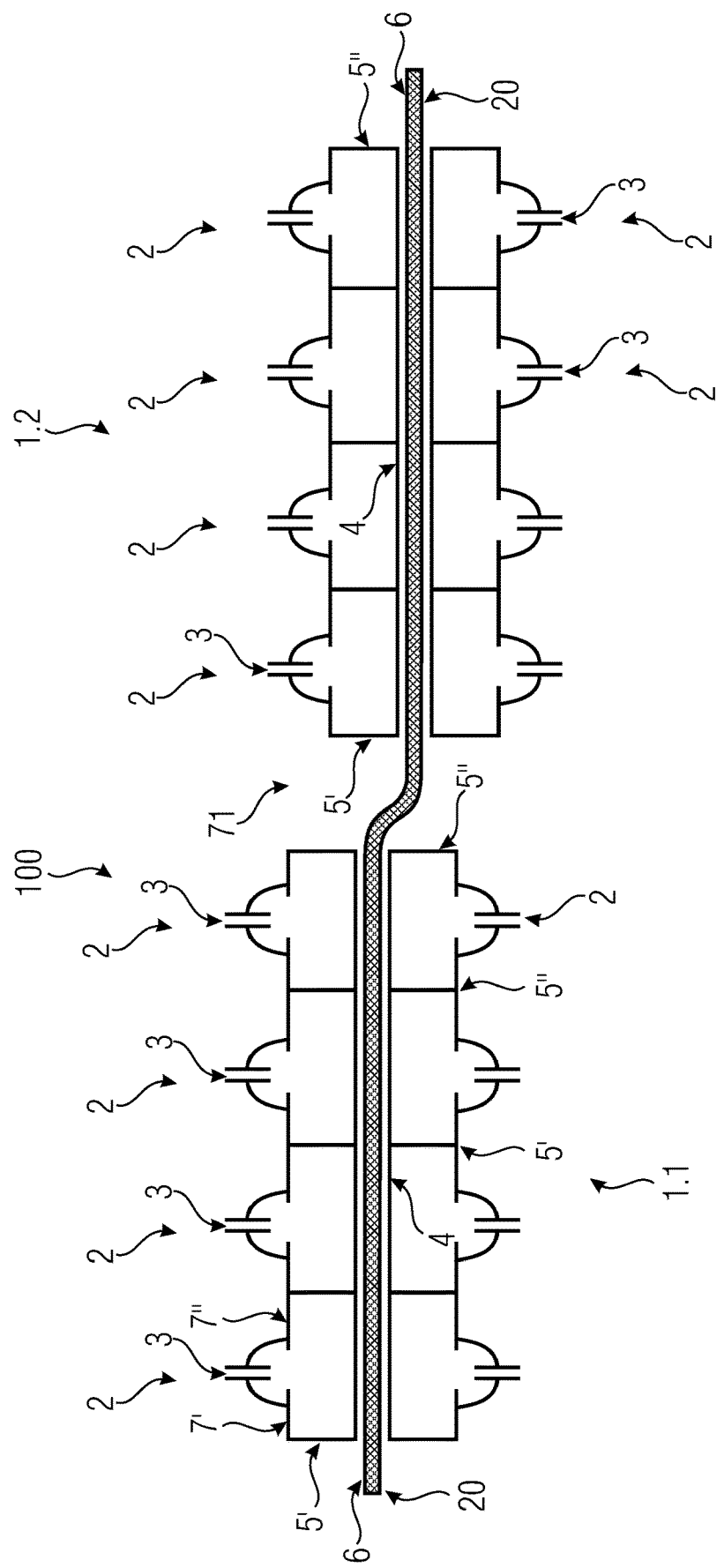
FIG. 4 illustrates a second embodiment of a cable arrangement according to the invention in a schematic view.

FIG. 4 illustrates a second embodiment of a cable arrangement 100 according to the invention in a schematic view.

In FIG. 4 a schematic diagram of an alternative for the advantageous embodiment of the invention is shown. The configuration of this cable mantle 1 is similar as described in FIG. 3 except that the shielded cable 20 is partially covered by a first cable mantle 1.1 and partially covered by a second cable mantle 1.2 leaving a segment 71 of the cable 20 without coverage.

Figure 5:
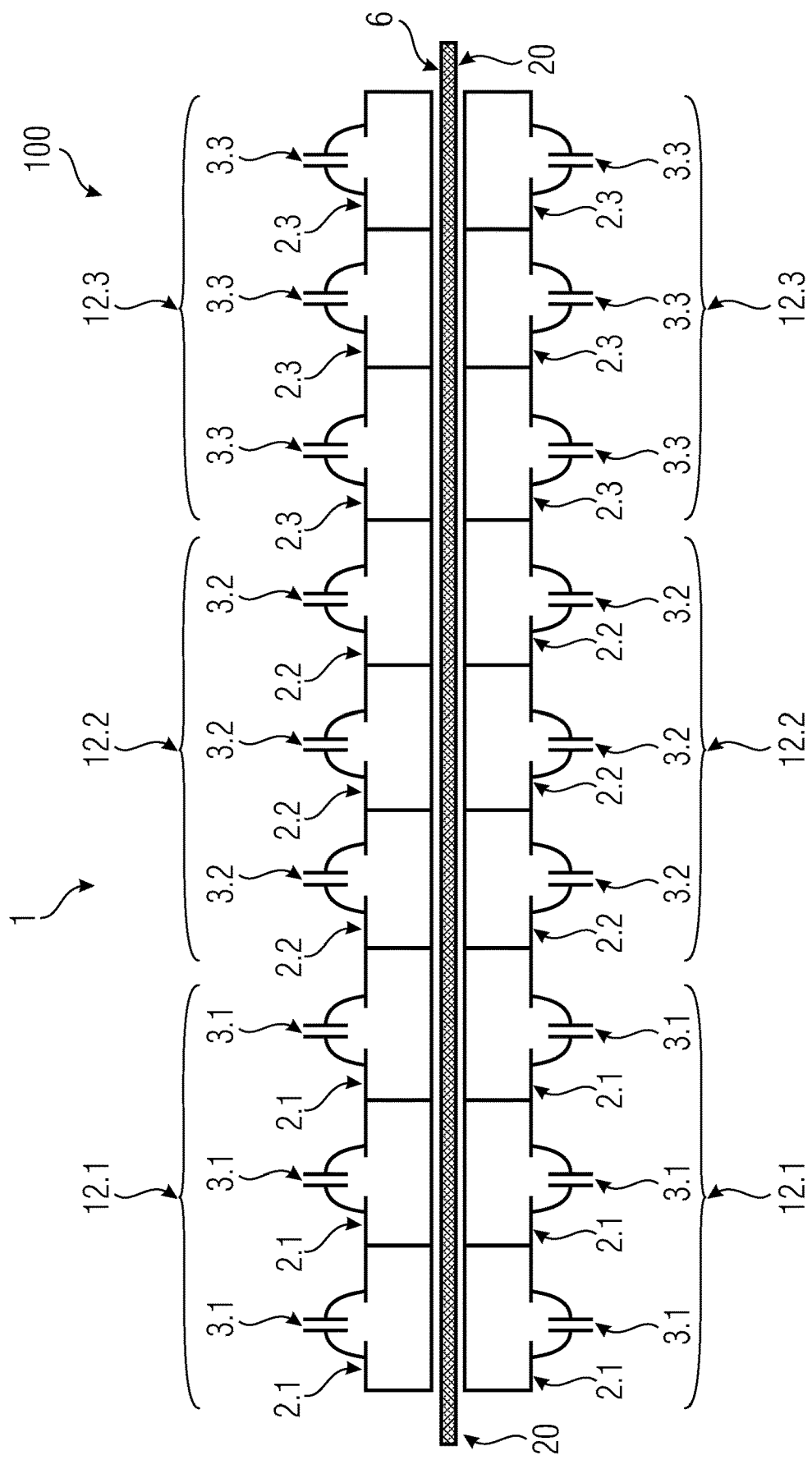
FIG. 5 illustrates a third embodiment of a cable arrangement according to the invention in a schematic view.

FIG. 5 illustrates a third embodiment of a cable arrangement 100 according to the invention in a schematic view.

According to some embodiments the resonant elements 2 of the cable mantle 1 are grouped into a plurality of resonant element groups 12, wherein the resonance frequencies of all of the resonant elements 2 of one of the resonant element groups 12 are equal, wherein the resonance frequencies of the resonant elements 2 of one of the resonant element groups 12 are different from the resonance frequencies of the resonant elements 2 of one other of the resonant element groups 12.

In FIG. 5 a schematic diagram for an alternative embodiment for multi-frequency response behavior is presented. Herein, the cable mantle 1 is composed of a multitude of different resonant elements 2.1, 2.2, 2.3 covering completely or partially a shielded cable 20, wherein all resonant elements 2.1 have a first resonance frequency, all resonant elements 2.2 have a second resonance frequency and all resonant elements 2.3 have a third resonance frequency, wherein the first resonance frequency, the second resonance frequency and the third resonance frequency are different from each other. The resonant elements 2.1, 2.2, 2.3 are grouped in resonant element groups 12.1, 12.2 and 12.3, wherein the resonant element group 12.1 comprises the resonant elements 2.1 having the first resonance frequency, wherein the resonant element group 12.2 comprises the resonant elements 2.2 having the second resonance frequency, and wherein the resonant element group 12.3 comprises the resonant elements 2.3 having the third resonance frequency so that each resonant element groups 12.1, 12.2, 12.3 is resonant at different frequencies by changing, for example, the associated capacitances 3.1, 3.2, 3.3.

Figure 6:
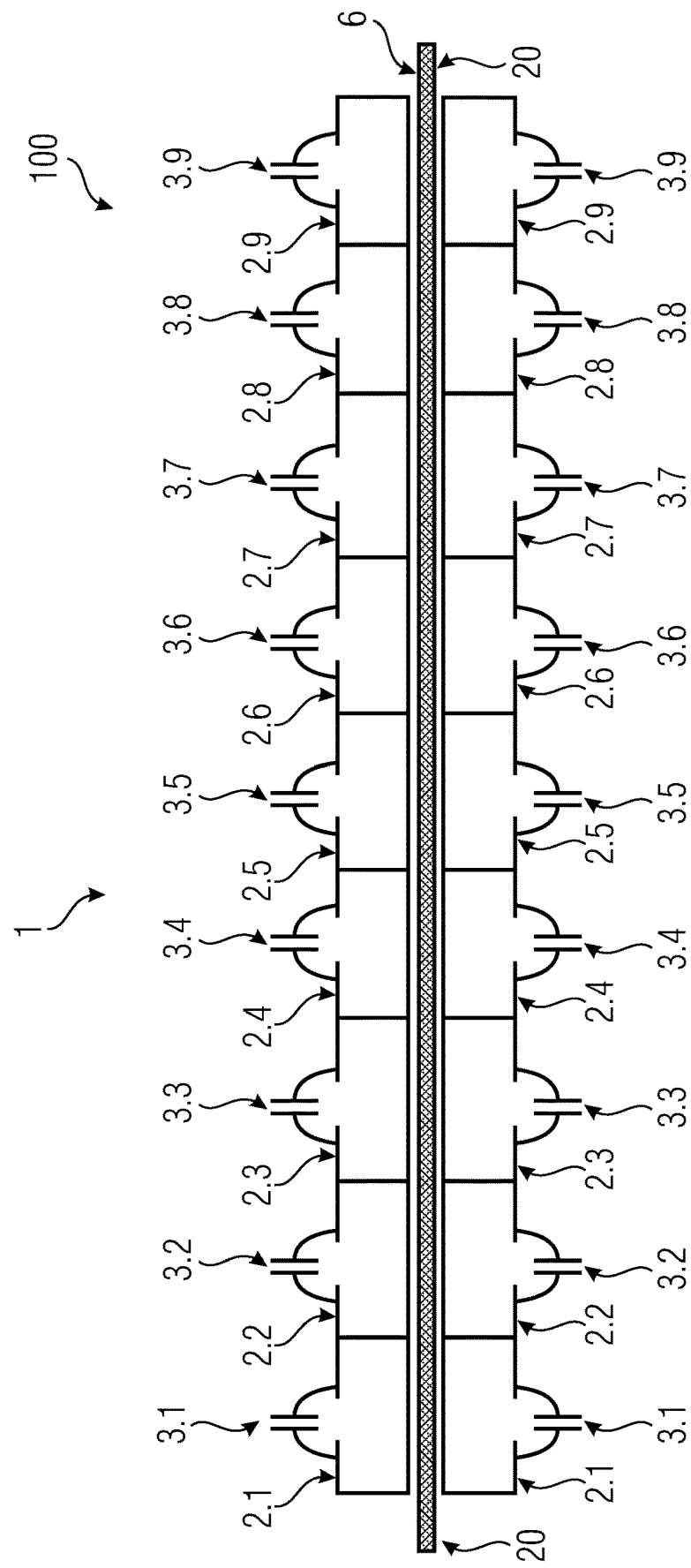
FIG. 6 illustrates a fourth embodiment of a cable arrangement according to the invention in a schematic view.

FIG. 6 illustrates a fourth embodiment of a cable arrangement 100 according to the invention in a schematic view.

According to some embodiments the resonance frequencies of at least some of the resonant elements 2 of the cable mantle are different, wherein the resonance frequencies of all of the resonant elements 2 are distributed around a center resonance frequency with a maximum deviation of plus or minus 5%.

In FIG. 6 a schematic diagram for an alternative embodiment for broad bandwidth response behavior is presented. Herein, the cable mantle 1 is composed of a multitude of resonant elements 2.1 to 2.9 covering completely or partially a cable 20. The resonant elements 2.1 to 2.9 resonate close to center resonance frequency. However, the resonant frequencies of the resonant elements 2 differ slightly from each other, so that a broad-bandwidth behavior is created. This may be achieved by using different capacitance values for the capacitors 3.1 to 3.9 associated with the resonant elements 2.1 to 2.9. The capacitance shift is a fraction of a center capacitance value (e.g. a few pF) used to tune resonant elements 2.1 to 2.9 to the center resonant frequency.

Figure 7:
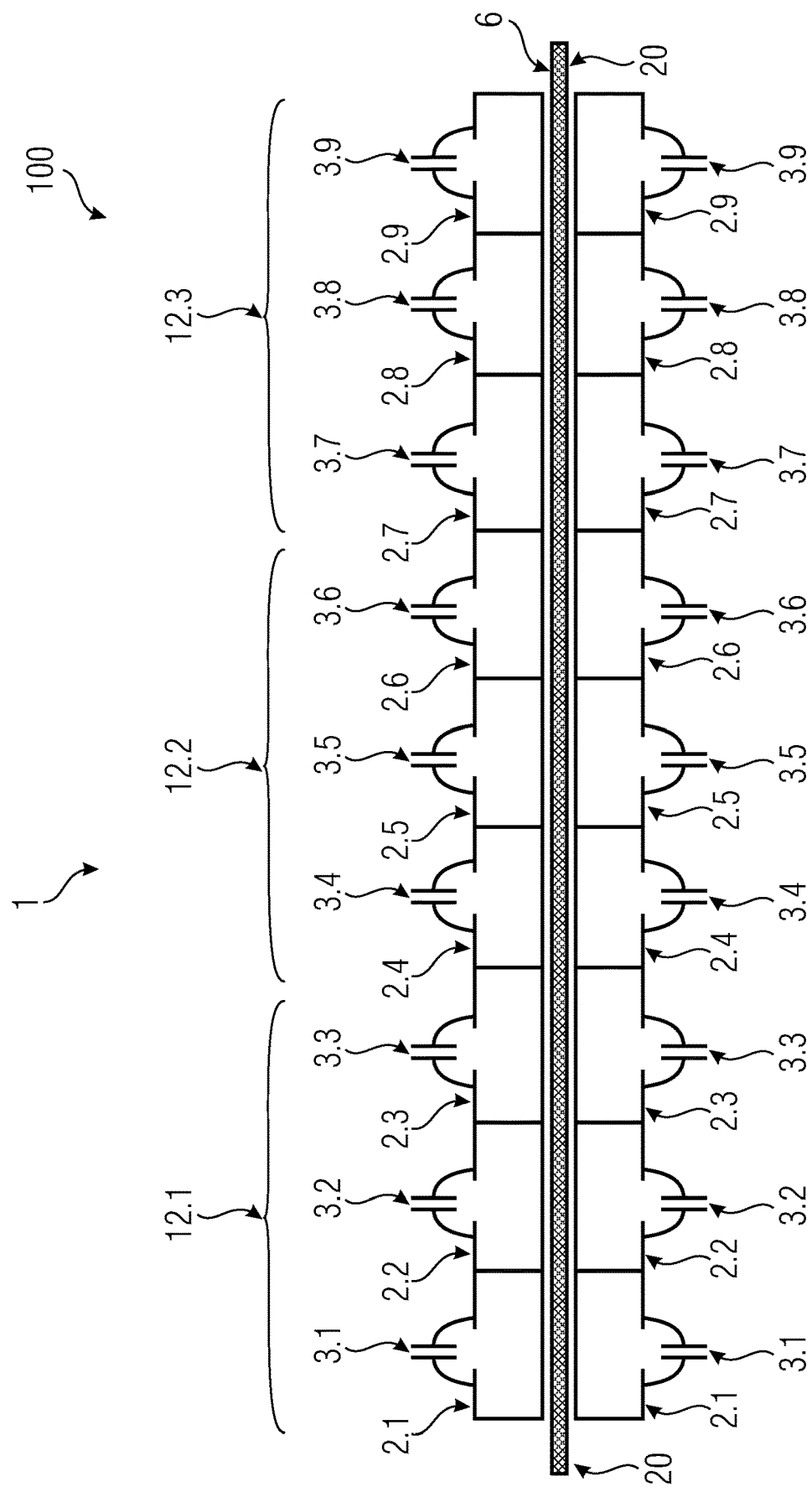
FIG. 7 illustrates a fifth embodiment of a cable arrangement according to the invention in a schematic view.

FIG. 7 illustrates a fifth embodiment of a cable arrangement 100 according to the invention in a schematic view.

According to some embodiments the resonant elements 2 are grouped into a plurality of resonant element groups 12, wherein the resonance frequencies of at least some of the resonant elements 2 within each of the resonant element groups 12 are different, wherein the resonance frequencies of the resonant elements 2 within each of the resonant element groups 12 are distributed around a center resonance frequency with a maximum deviation of plus or minus 5%, wherein the center resonance frequency of at least one of the resonant element groups 12 is different from the center resonance frequency of one other of the resonant element groups 12.

In FIG. 7 a schematic diagram for an alternative embodiment for multi-frequency and broad-bandwidth response behavior is presented. Herein, the cable mantle 1 is composed of a multitude of dissimilar resonant elements 2.1 to 2.9 covering completely or partially a cable 20. The resonant elements 2.1 to 2.9 are grouped in resonant element groups 12.1, 12.2 and 12.3, which have different center resonance frequencies. Thus, the resonant elements 2.1 to 2.9 of the resonant element groups 12.1, 12.2 and 12.3 resonate close to different center resonance frequencies creating a multi-frequency behavior as explained in the context of FIG. 5. In addition to the multi-frequency behavior, a broad bandwidth behavior is achieved as explained in context of FIG. 6. This may be achieved by an appropriate selection of the capacitance values for the capacitors 3.1 to 3.9 associated with each unit resonant elements 2.1 to 2.9.

Figure 8:
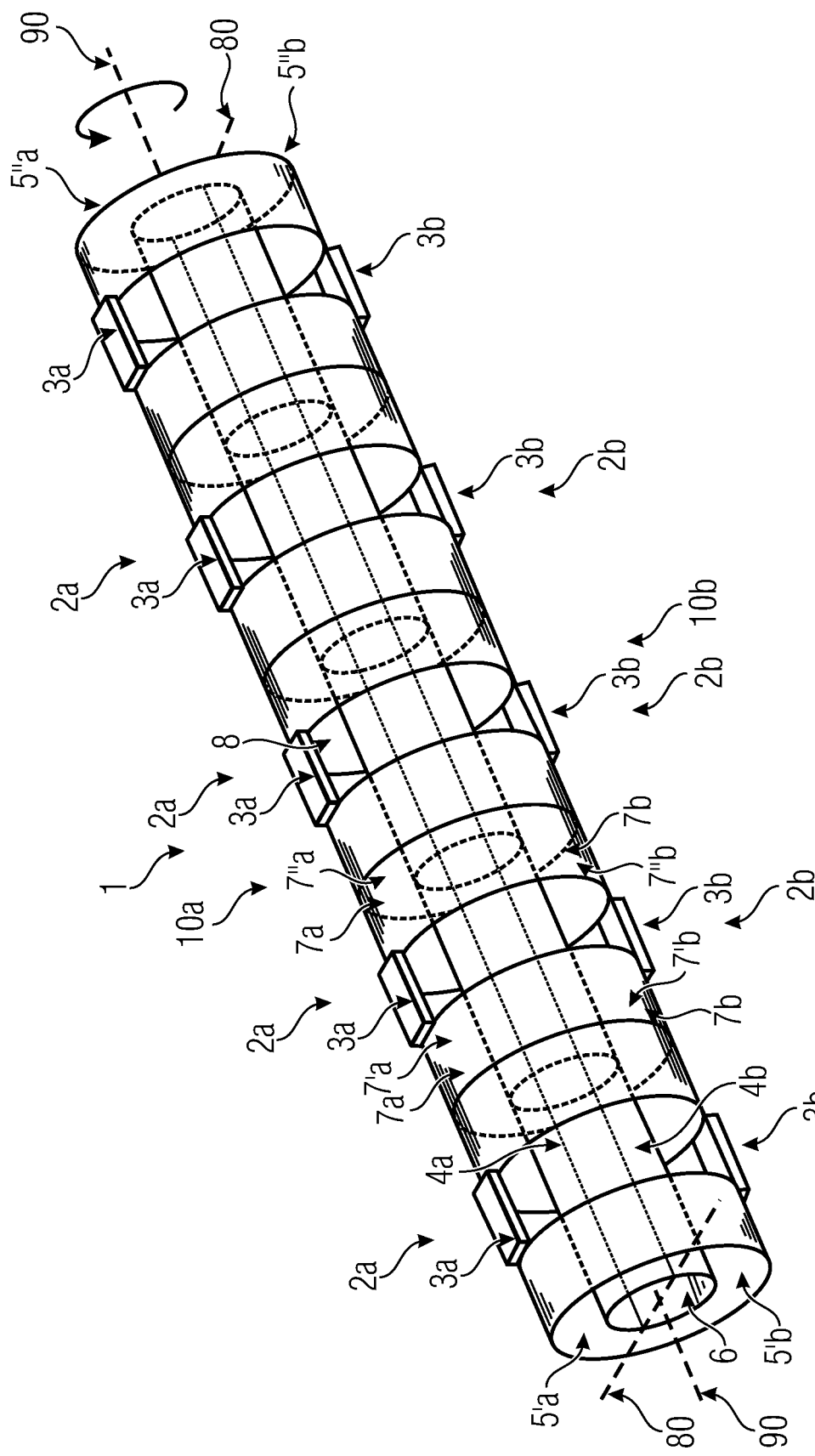
FIG. 8 illustrates a further embodiment of a cable mantle according to the invention in a schematic three-dimensional view.

FIG. 8 illustrates a further embodiment of a cable mantle 1 according to the invention in a schematic three-dimensional view.

According to some embodiments the cable mantle 1 comprises a first construction group 10a and a second construction group 10b, wherein the first construction group 10a and the second construction group 10b are connectable to each other in a detachable way, wherein the shielded cable 20 can be transversally moved into the cable mantle 1 or transversally removed from the cable mantle 1 respectively when the first construction group 10a and the second construction group 10b are detached from each other.

The advantageous embodiment of the cable mantle shown in FIG. 8 implies a detachable function which is performed by splitting the cable mantle 1 into construction groups 10a and 10b. The splitting plane is defined by the longitudinal axis 90 and the transversal axis 80. Each part 2a, 2b of one of the resonant elements 2 contains a part 4a, 4b of an inner tube-shaped conductive structure 4 and a part 7a, 7b of an outer tube-shaped conductive structure 7, wherein the parts 4a and 4b are connected with the parts 7'a and 7'b via the parts 5'a and 5'b of the first transversal conductive structure 5', and wherein the parts 4a and 4b are connected with the parts 7"a and 7"b via the parts 5"a and 5"b of the second transversal conductive structure 5". When assembled as shown, the cable mantle 1 can host internally a shielded cable in the through hole 6.

Figure 9:
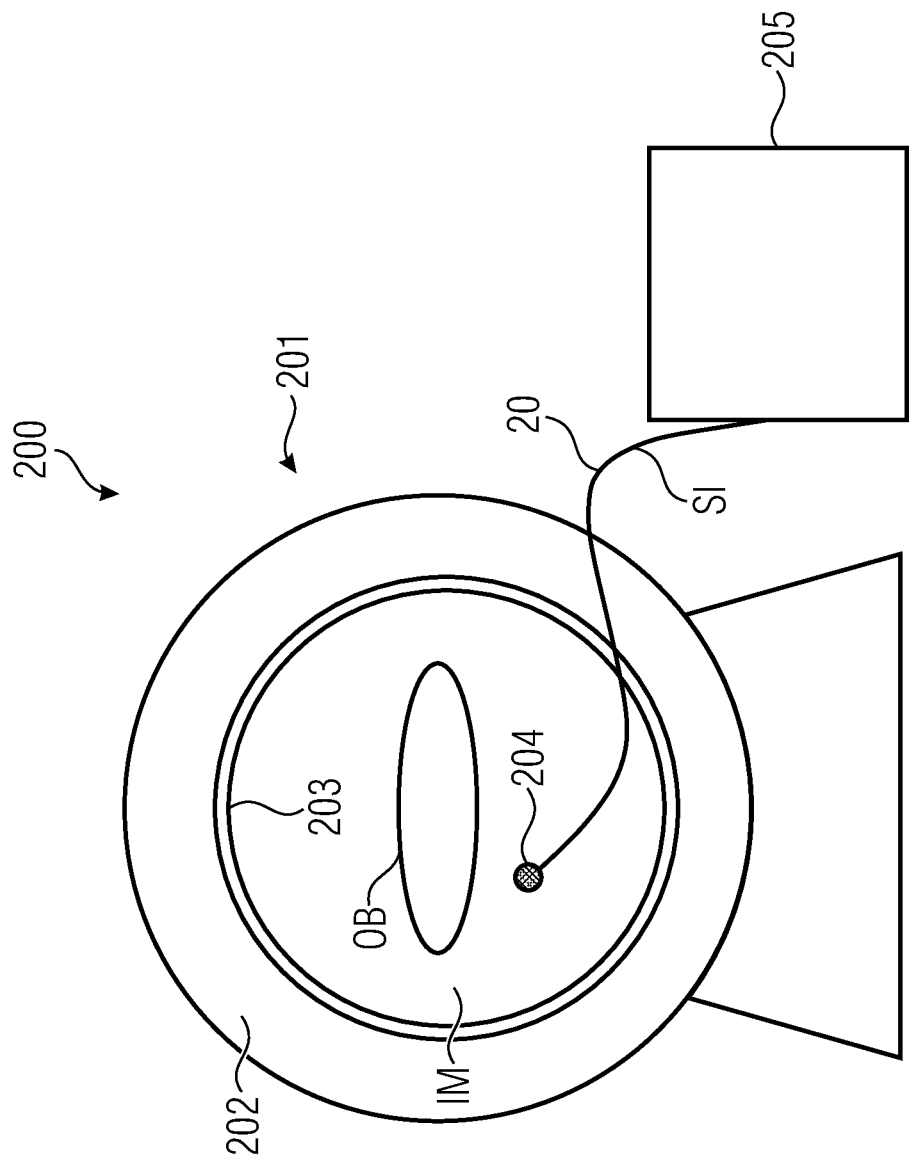
FIG. 9 illustrates an embodiment of a system for examining an object according to the invention in a schematic view.

FIG. 9 illustrates an embodiment of a system 200 for examining an object OB according to the invention in a schematic view.

The system 200 comprises a magnetic resonance imaging scanner 201 for a production of a magnetic resonance image of the object OB in an imaging volume IM, wherein the magnetic resonance imaging scanner 201 comprises a magnet assembly 202 for applying a static magnetic field to the imaging volume IM during the production of the magnetic resonance image, wherein the magnetic resonance imaging scanner 201 comprises a radiofrequency coil assembly 203 for applying a radiofrequency magnetic field to the imaging volume IM during the production of the magnetic resonance image, wherein the system 200 comprises a monitoring device 20, 204, 205 for monitoring the object OB in the imaging volume IM during the production of the magnetic resonance image, wherein the monitoring device 20, 204, 205 comprises a sensing unit 204, an evaluating unit 205 and a cable arrangement 20, wherein the sensing unit 204 is configured for producing sensing signals SI related to the object OB during the production of the magnetic resonance image while being arranged within the imaging volume IM, wherein the evaluating unit 205 is configured for evaluating the sensing signals SI, wherein the sensing signals SI are transmitted from the sensing unit 204 to the evaluating unit 205 by the cable arrangement 20, wherein the cable arrangement 20 is configured according to the invention.

Figure 10:
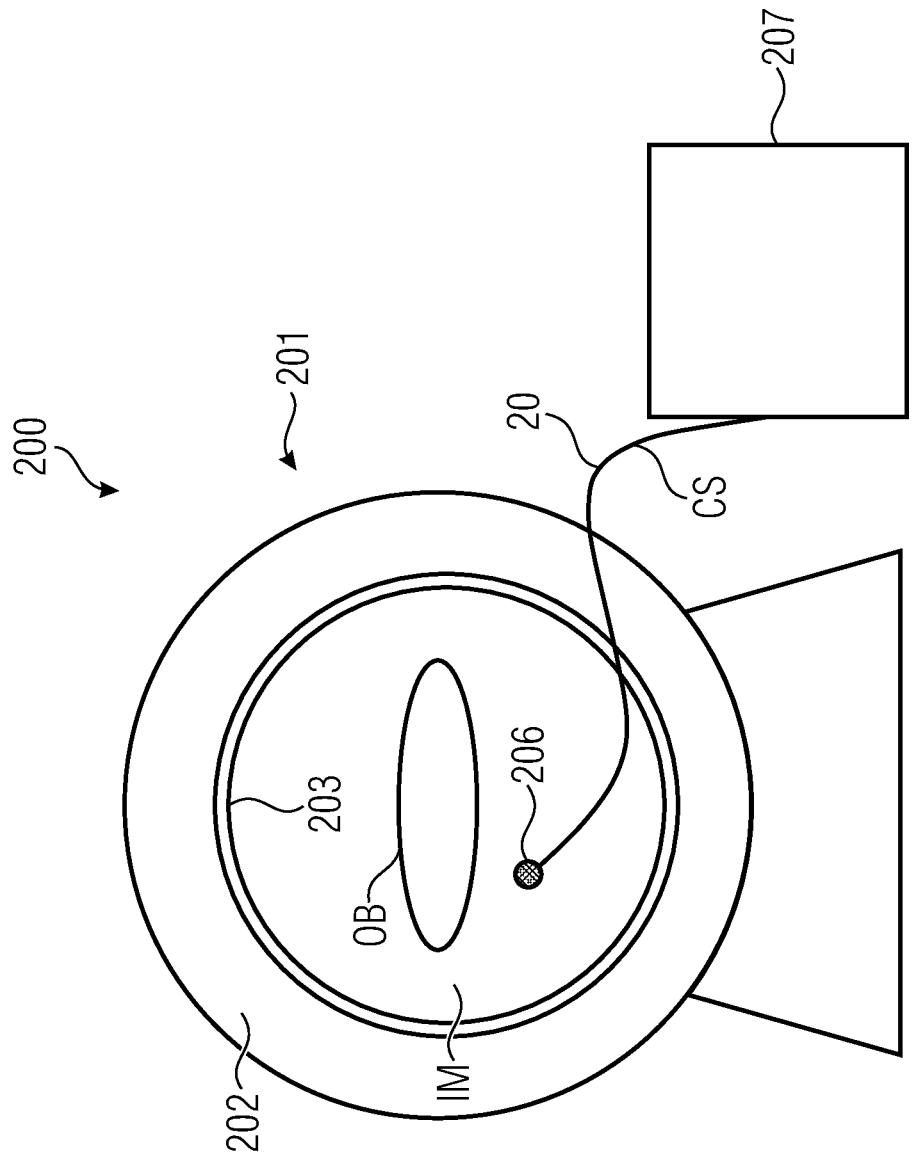
FIG. 10 illustrates a further embodiment of a system for examining an object according to the invention in a schematic view.

FIG. 10 illustrates a further embodiment of a system 200 for examining an object OB according to the invention in a schematic view.

The system 200 comprises a magnetic resonance imaging scanner 201 for a production of a magnetic resonance image of the object OB in an imaging volume IM, wherein the magnetic resonance imaging scanner 201 comprises a magnet assembly 202 for applying a static magnetic field to the imaging volume IM during the production of the magnetic resonance image, wherein the magnetic resonance imaging scanner 201 comprises a radiofrequency coil assembly 203 for applying a radiofrequency magnetic field to the imaging volume IM during the production of the magnetic resonance image, wherein the system 200 comprises a treating device 20, 206, 207 for treating the object OB in the imaging volume IM during the production of the magnetic resonance image, wherein the treating device 20, 206, 207 comprises an actuator unit 206, a control unit 207 and a cable arrangement 20, wherein the control unit 207 is configured for producing control signals CS, wherein the actuator unit 206 is configured for applying energy to the object OB during the production of the magnetic resonance image while being arranged within the imaging volume IM depending on the control signals CS, wherein the control signals CS are transmitted from the control unit 207 to the actuator unit 206 by the cable arrangement 20, wherein the cable arrangement 20 is configured as specified above.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A cable mantle, comprising:
   a through hole along a longitudinal direction of the cable mantle, wherein the through hole is configured for hosting a shielded cable; and
   a plurality of resonant elements arranged along the longitudinal direction of the cable mantle, wherein the plurality of resonant elements is configured for shield current suppression in the shielded cable;
   wherein each of the resonant elements comprises
   an inner tube-shaped conductive structure, which extends in the longitudinal direction between a first end section of the resonant element and a second end section of the resonant element, and which surrounds in a circumferential direction a longitudinal portion of the through hole;
   an outer tube-shaped conductive structure, which extends in the longitudinal direction between the first end section of the resonant element and the second end section of the resonant element, and which surrounds in the circumferential direction a longitudinal portion of the inner tube-shaped conductive structure, wherein the outer tube-shaped conductive structure comprises a circumferential gap so that a first longitudinal portion of the outer tube-shaped conductive structure is separated from a second longitudinal portion of the outer tube-shaped conductive structure;
   a first transversal conductive structure, which connects the inner tube-shaped conductive structure and the first longitudinal portion of the outer tube-shaped conductive structure at the first end section of the resonant element;
   a second transversal conductive structure, which connects the inner tube-shaped conductive structure and the second longitudinal portion of the outer tube-shaped conductive structure at the second end section of the resonant element; and
   at least one capacitor bridging the gap between the first longitudinal portion of the outer tube-shaped conductive structure and the second longitudinal portion of the outer tube-shaped conductive structure, so that an electrical behavior of the inner tube-shaped conductive structure, the first longitudinal portion of the outer tube-shaped conductive structure, the second longitudinal portion of the outer tube-shaped conductive structure, the first transversal conductive structure, the second transversal conductive structure and the at least one capacitor is equivalent to a parallel resonant circuit defining a resonance frequency of the respective resonant element.

2. The cable mantle according to claim 1, wherein the resonant elements are arranged in a repetitive pattern, wherein a step size of the repetitive pattern is shorter than wavelengths corresponding to the resonance frequencies of the resonant elements.

3. The cable mantle according to claim 1, wherein the resonance frequencies of all of the resonant elements are equal.

4. The cable mantle according to claim 1, wherein the resonant elements are grouped into a plurality of resonant element groups, wherein the resonance frequencies of all of the resonant elements of one of the resonant element groups are equal, wherein the resonance frequencies of the resonant elements of one of the resonant element groups are different from the resonance frequencies of the resonant elements of one other of the resonant element groups.

5. The cable mantle according to claim 1, wherein the resonance frequencies of at least some of the resonant elements are different, wherein the resonance frequencies of all of the resonant elements are distributed around a center resonance frequency with a maximum deviation of plus or minus 5%.

6. The cable mantle according to claim 1, wherein the resonant elements are grouped into a plurality of resonant element groups, wherein the resonance frequencies of at least some of the resonant elements within each of the resonant element groups are different, wherein the resonance frequencies of the resonant elements within each of the resonant element groups are distributed around a center resonance frequency with a maximum deviation of plus or minus 5%, wherein the center resonance frequency of at least one of the resonant element groups is different from the center resonance frequency of one other of the resonant element groups.

7. The cable mantle according to claim 1, wherein the at least one capacitor of one of the resonant elements is a variable capacitor.

8. The cable mantle according to claim 1, wherein the cable mantle comprises a first construction group and a second construction group, wherein the first construction group and the second construction group are connectable to each other in a detachable way, wherein the shielded cable can be transversally moved into the cable mantle or transversally removed from the cable mantle respectively when the first construction group and the second construction group are detached from each other.

9. The cable mantle according to claim 1, wherein at least some neighboring resonant elements of the plurality of resonant elements are spaced apart from each other.

10. A cable arrangement comprising:
    a shielded cable comprising at least one conductive center wire and a conductive shield shielding the at least one conductive center wire, wherein the at least one conductive center wire is isolated from the conductive shield; and
    at least one cable mantle, comprising:
    a through hole along a longitudinal direction of the cable mantle, wherein the shielded cable is hosted in the through hole; and
    a plurality of resonant elements arranged along the longitudinal direction of the cable mantle, wherein the plurality of resonant elements is configured for shield cur-rent suppression in the shielded cable;
    wherein each of the resonant elements comprises an inner tube-shaped conductive structure, which extends in the longitudinal direction between a first end section of the resonant element and a second end section of the resonant element, and which surrounds in a circumferential direction a longitudinal portion of the through hole;

an outer tube-shaped conductive structure, which extends in the longitudinal direction between the first end section of the resonant element and the second end section of the resonant element, and which surrounds in the circumferential direction a longitudinal portion of the inner tube-shaped conductive structure, wherein the outer tube-shaped conductive structure comprises a circumferential gap so that a first longitudinal portion of the outer tube-shaped conductive structure is separated from a second longitudinal portion of the outer tube-shaped conductive structure;

a first transversal conductive structure, which connects the inner tube-shaped conductive structure and the first longitudinal portion of the outer tube-shaped conductive structure at the first end section of the resonant element;

a second transversal conductive structure, which connects the inner tube-shaped conductive structure and the second longitudinal portion of the outer tube-shaped conductive structure at the second end section of the resonant element; and at least one capacitor bridging the gap between the first longitudinal portion of the outer tube-shaped conductive structure and the second longitudinal portion of the outer tube-shaped conductive structure, so that an electrical behavior of the inner tube-shaped conductive structure, the first longitudinal portion of the outer tube-shaped conductive structure, the second longitudinal portion of the outer tube-shaped conductive structure, the first transversal conductive structure, the second transversal conductive structure and the at least one capacitor is equivalent to a parallel resonant circuit defining a resonance frequency of the respective resonant element.

11. The cable arrangement according to claim 10, wherein the at least one conductive center wire and the conductive shield of the shielded cable are insulated from the plurality of resonant elements of the at least one cable mantle.

12. System for examining an object, wherein the system comprises a magnetic resonance imaging scanner for a production of a magnetic resonance image of the object in an imaging volume, wherein the magnetic resonance imaging scanner comprises a magnet assembly for applying a static magnetic field to the imaging volume during the production of the magnetic resonance image, wherein the magnetic resonance imaging scanner comprises a radiofrequency coil assembly for applying a radiofrequency magnetic field to the imaging volume during the production of the magnetic resonance image, wherein the system comprises a monitoring device for monitoring the object in the imaging volume during the production of the magnetic resonance image, wherein the monitoring device comprises a sensing unit, an evaluating unit and a cable arrangement, wherein the sensing unit is configured for producing sensing signals related to the object during the production of the magnetic resonance image while being arranged within the imaging volume, wherein the evaluating unit is configured for evaluating the sensing signals, wherein the sensing signals are transmitted from the sensing unit to the evaluating unit by the cable arrangement, wherein the cable arrangement is configured according to claim 10.

13. System for examining an object, wherein the system comprises a magnetic resonance imaging scanner for a production of a magnetic resonance image of the object in an imaging volume, wherein the magnetic resonance imaging scanner comprises a magnet assembly for applying a static magnetic field to the imaging volume during the production of the magnetic resonance image, wherein the magnetic resonance imaging scanner comprises a radiofrequency coil assembly for applying a radiofrequency magnetic field to the imaging volume during the production of the magnetic resonance image, wherein the system comprises a treating device for treating the object in the imaging volume during the production of the magnetic resonance image, wherein the treating device comprises an actuator unit, a control unit and a cable arrangement, wherein the control unit is configured for producing control signals, wherein the actuator unit is configured for applying energy to the object during the production of the magnetic resonance image while being arranged within the imaging volume depending on the control signals, wherein the control signals are transmitted from the control unit to the actuator unit by the cable arrangement, wherein the cable arrangement is configured according to claim 10.

* * * * *